(12) United States Patent
Hook et al.

(10) Patent No.: US 8,616,125 B2
(45) Date of Patent: Dec. 31, 2013

(54) COMPLIANT EMBOSSER ASSEMBLY

(75) Inventors: Jeremy Frederic Hook, Cincinnati, OH (US); Jeremy Robert Basham, Cincinnati, OH (US); James Arthur Keighley, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 327 days.

(21) Appl. No.: 11/384,699

(22) Filed: Mar. 20, 2006

(65) Prior Publication Data
US 2007/0214973 A1 Sep. 20, 2007

(51) Int. Cl.
*B41F 19/02* (2006.01)
*B31F 1/07* (2006.01)
*B44B 5/02* (2006.01)

(52) U.S. Cl.
USPC .................................. 101/23; 101/7

(58) Field of Classification Search
USPC ............... 101/3.1, 4, 5, 6, 7, 22, 23, 28, 32
See application file for complete search history.

(56) References Cited

U.S. PATENT DOCUMENTS

| | | | |
|---|---|---|---|
| 1,368,956 A * | 2/1921 | Merey | 101/3.1 |
| 1,528,956 A | 3/1925 | Smith | |
| 2,094,268 A * | 9/1937 | Friedman | 239/33 |
| 2,966,723 A | 1/1961 | Swope | |
| 3,264,978 A | 8/1966 | Staley | |
| 3,667,265 A * | 6/1972 | Zippe | 72/84 |
| 3,815,493 A * | 6/1974 | Broderick | 101/6 |
| 3,877,919 A | 4/1975 | Shorr | |
| 4,073,208 A * | 2/1978 | Kirkpatrick | 83/659 |
| 4,823,450 A | 4/1989 | Ramisch et al. | |
| 5,167,897 A | 12/1992 | Weber et al. | |
| 5,238,642 A * | 8/1993 | Benquet et al. | 264/284 |
| 5,308,346 A | 5/1994 | Sneller et al. | |
| 5,411,463 A | 5/1995 | Brookstein | |
| 5,830,296 A | 11/1998 | Emenaker et al. | |

(Continued)

FOREIGN PATENT DOCUMENTS

| | | |
|---|---|---|
| EP | 0 551 758 | 7/1993 |
| EP | 0 763 667 | 3/1997 |

(Continued)

OTHER PUBLICATIONS

PCT International Search Report dated Oct. 19, 2007, 7 pages.

*Primary Examiner* — Ren Yan
*Assistant Examiner* — Leo T Hinze
(74) *Attorney, Agent, or Firm* — Wednesday G. Shipp; Sarah M. DeCristofaro; Roddy M. Bullock (57) ABSTRACT

An embossing assembly for forming an embossment pattern on a tube blank having a first roll and a second roll. The first roll includes a first shaft having a first axis of rotation and an embossing element joined to the first shaft. The second roll is configured to engage a tube blank when the tube blank at partially surrounds the first roll. The second roll includes a second shaft and a hub joined to the second shaft. The hub includes an engagement region configured to apply pressure to a tube blank adjacent to the embossing element thereby causing part of the tube blank to at least partially conform to the shape of the embossing element. The engagement region includes a compliant material which is more compliant than the second shaft thereby allowing the engagement region to compensate for variations in a wall thickness of a tube blank.

13 Claims, 7 Drawing Sheets

(56) References Cited

U.S. PATENT DOCUMENTS

| | | |
|---|---|---|
| 6,170,393 B1 | 1/2001 | Hook et al. |
| 6,520,896 B1 * | 2/2003 | Sohl ................................ 492/45 |
| 6,610,025 B2 | 8/2003 | Berg et al. |
| 6,729,869 B2 * | 5/2004 | Lofink ........................... 425/363 |
| 6,958,057 B2 | 10/2005 | Berg, Jr. et al. |
| 7,066,870 B2 * | 6/2006 | Fedyk et al. ................... 493/156 |
| 7,736,287 B2 * | 6/2010 | Song et al. .................... 493/156 |
| 2003/0236499 A1 | 12/2003 | Fedyk et al. |

FOREIGN PATENT DOCUMENTS

| | | |
|---|---|---|
| WO | WO 9959512 | 11/1999 |
| WO | WO 2004/108037 | 12/2004 |
| WO | WO 2006/055794 | 5/2006 |

* cited by examiner

COMPLIANT EMBOSSER ASSEMBLY

FIELD OF THE INVENTION

This invention relates to an apparatus for embossing a pattern onto an applicator for disposable absorbent articles. More particularly, the present invention relates to an embosser assembly which may compensate for variations in material thickness, may reduce vibrations associated with the embossing assembly and may improve the embossing line process and/or embossing quality.

BACKGROUND OF THE INVENTION

Disposable absorbent articles utilized to absorb menses are well known. An example of such a disposable absorbent article which has gained much popularity is the disposable tampon.

In order to facilitate the insertion of the tampon into the body, tampons are often packaged with a tampon applicator. In general, the applicator includes an insertion tube and a plunger tube which is telescopically associated with the insertion tube. The insertion tube typically comprises an insertion end and a removal end. The tampon is typically disposed in the insertion tube and is inserted into the body from the insertion end of the insertion tube. The tampon is typically oriented within the insertion tube such that a removal string, which is joined to an end of the tampon extends, through the plunger tube of the applicator.

For the purpose of inserting the tampon into the body, the plunger tube is typically depressed such that the plunger tube translates from about the removal end of the insertion tube to about the insertion end of the insertion tube, thereby forcing the tampon out of the applicator and into the body. Without the plunger tube, insertion of the tampon into the body can be difficult and/or problematic.

A problem with some conventional applicators is that the plunger tube can fall out of the insertion tube. Typically, the plunger tube can be placed back into the opening of the insertion tube; however, the removal string of the tampon generally has to be threaded back through the plunger tube prior to insertion of the tampon into the body. However, the threading of the removal string back through the plunger tube can be difficult because the removal string is generally not a rigid element. In addition, some wearers may be reluctant to place the plunger tube back into the insertion tube after it has fallen out of the insertion tube.

Consequently, a need exists for an apparatus which can produce a plunger tube having a reduced likelihood of becoming disengaged with an insertion tube. Additionally, a need exists for a method of making a plunger tube which has a reduced likelihood of becoming disengaged with an insertion tube.

SUMMARY OF THE INVENTION

The present invention provides an apparatus which can produce a plunger tube having a reduced likelihood of falling out of an insertion tube and a method for making the plunger tube. In one embodiment, the apparatus includes an embossing assembly for forming an embossment pattern on a tube blank. In some embodiments, the embossing assembly comprises a first roll and a second roll. The first roll comprises a first shaft and an embossing element joined to the first shaft. The embossing element and the first shaft are configured such that the tube blank can at least partially surround the first shaft and the embossing element.

The second roll comprises a second shaft and a hub joined to the second shaft. The second roll is configured to engage the tube blank. The hub comprises an engagement region joined to the second shaft. The engagement region comprises a compliant material which is more compliant than the second shaft, and the engagement region is configured to apply pressure to the tube blank adjacent to the embossing element thereby causing part of the tube blank to at least partially conform to the shape of the embossing element. The hub further comprises a non-engagement region joined to the second shaft.

In other embodiments, the embossing assembly includes the first roll and the second roll as described above. Additionally, the first roll has a first axis of rotation, and the second roll has a second axis of rotation. The first axis of rotation and the second axis of rotation are generally parallel. Additionally, the compliant material may have a durometer of about 75 Shore D.

In some embodiments, the hub comprises an inner support, a compliant material, an outer support, and inner lateral stabilizers. The inner support can be joined to and disposed outward from the second shaft. The compliant material can be joined to and disposed outward from the inner support. The compliant material can have a durometer of about 95 Shore A. The outer support can be joined to and disposed outward from the compliant material and may comprise a pair of shoulders and an engaging surface. The embossing element is received between the shoulders. The inner lateral stabilizer may extend from the compliant material inward through the inner support.

DETAILED DESCRIPTION OF THE INVENTION

Definitions:

As used herein the term "compliant" is used to describe materials which compresses under a given load. A first material which is more "compliant" than a second material compresses under a first load which is less than a second load under which the second material compresses. The second material does not compress under the first load to the same extent as the first material.

As used herein the term "joined" encompasses configurations whereby an element is directly secured to another element by affixing the element directly to the other element, and configurations whereby an element is indirectly secured to another element by affixing the element to an intermediate member(s) which in turn are affixed to the other element.

Description:

This invention relates to an apparatus for embossing a pattern onto applicators for disposable absorbent articles such as tampons. However, the apparatus of the present invention can be utilized in any embossing assembly where a desire to improve the embossing line process and the embossing line quality exist. Additionally, the present invention relates to a method of making a plunger tube which has a reduced likelihood of becoming disengaged with an insertion tube.

Figure 1:
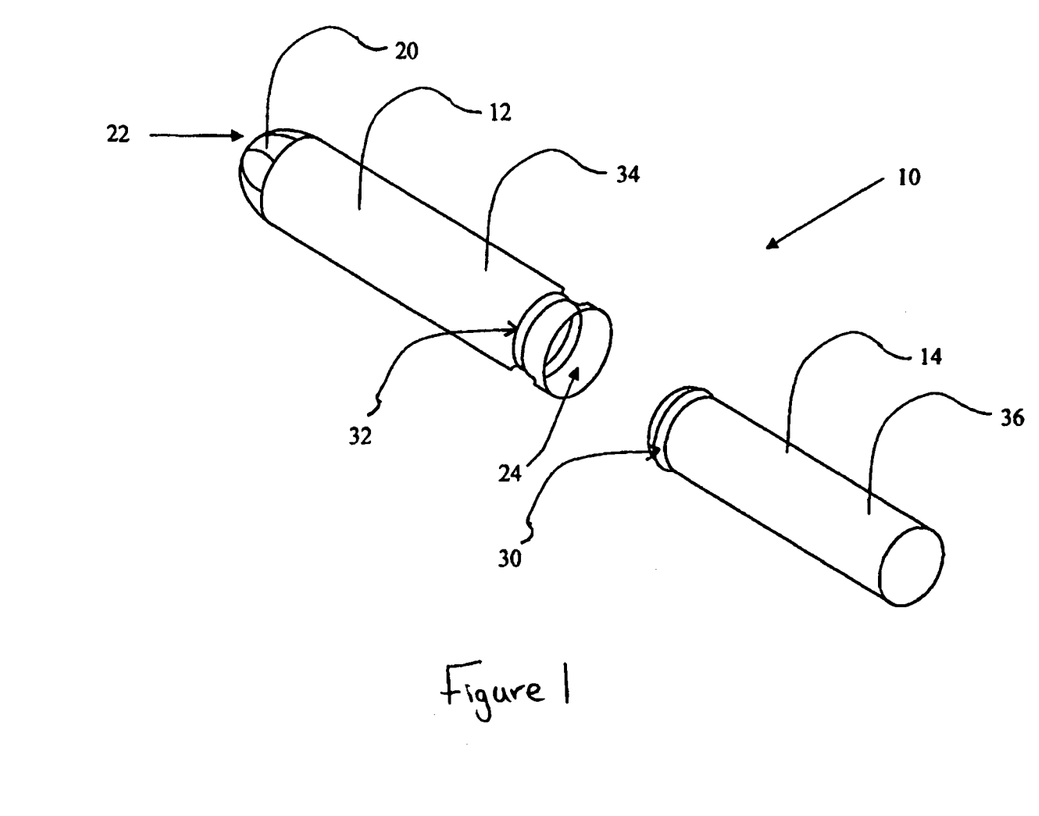
FIG. 1 is an isometric view showing an applicator for a disposable absorbent article, the applicator having an insertion tube and a plunger tube.

As shown in FIG. 1, an applicator 10, constructed in accordance with the present invention, may comprise an insertion tube 12 and a plunger tube 14. The insertion tube 12 may comprise an insertion end 22 and a removal end 24. The insertion end 22 may be configured in any suitable manner. For example, in some embodiments, the insertion end 22 may comprise a film cap 20 which comprises a plurality of petals. Examples film caps 20 are discussed in U.S. Pat. Nos. 6,958,057 and 6,610,025. Other exemplary configurations of the insertion end 22 are discussed in U.S. Patent Application Publication No. US 2003/0236499 A1.

Adjacent the removal end 24, the insertion tube 12 may comprise an indented region 32 which protrudes inward from an outer surface 34 of the insertion tube 12, in some embodiments. Correspondingly, the plunger tube 14 may comprise an interlocking region 30 which protrudes outward from an outer surface 36 of the plunger tube 14, in some embodiments. In some embodiments, the indented region 32 may comprise grip elements which protrude outward from the indented region 32. Embodiments where the indented region 32 and the interlocking region 30 extend outward from their respective outer surfaces are contemplated. Embodiments where the indented region 32 and the interlocking region 30 extend inward from their respective outer surfaces are contemplated. Embodiments, where the indented region 32 extends inward while the interlocking region 30 extends outward or vice versa are contemplated.

In some embodiments, the indented region 32 can be disposed continuously about the circumference of the insertion tube 12. In other embodiments, the indented region 32 may comprise a plurality of discrete elements disposed about the circumference of the insertion tube 12. Similarly, the interlocking region 30 can be disposed continuously about the circumference of the plunger tube 14 in some embodiments. In other embodiments, the interlocking region 30 may comprise a plurality of discrete elements disposed about the circumference of the plunger tube 14. The indented region 32 may comprise any suitable shape which facilitates grasping/holding of the applicator 10.

The indented region 32 and the interlocking region 30 can be configured such that when the plunger tube 14 is inserted into the insertion tube 12, the interlocking region 30 engages the indented region 32. The interlocking region 30 may comprise any suitable shape which can engage the indented region 32 of the insertion tube 12.

The degree of engagement between the grip region 32 and the interlocking region 30 can be measured as a separation force between the insertion tube 12 and the plunger tube 14. Tube lock (separation force) is a measure of the peak force required to separate a plunger tube from an insertion tube. In general, at higher tube locks (see below) the likelihood of the plunger tube 14 becoming disengaged from the insertion tube 12 is reduced. In some embodiments, the tube lock can be greater than about 100 grams force. In some embodiments, an acceptable tube lock can be greater than or equal to about 250 grams force. In other embodiments, the tube lock can be greater than or equal to about 450 grams force. In some embodiments, the tube lock can be greater than or equal to about 600 grams force. In some embodiments, the tube lock can be in a range of greater than about 100 grams force to about 1000 grams force or any individual number within the range.

The insertion tube 12 can be formed from any suitable material. Some examples of suitable material include paper, paperboard, cardboard, or a combination thereof. The insertion tube 12 may also be injection molded or formed from flexible plastic, such as thermoformed from a plastic sheet or folded or wound from plastic film. The insertion tube 12 may also be formed from a combination of paper and plastic. In some embodiments, the insertion tube 12 can be fairly rigid and can have a relatively small diameter of about 10 mm to about 20 mm or any individual number within the range.

In general, the insertion tube 12 can have a wall having a predetermined thickness of about 0.1 mm to about 0.7 mm or any individual number within the range. The wall can be constructed from a single ply of material or can be formed from two or more plies that are bonded together to form a laminate. In some embodiments, when two or more plies are utilized, all the plies can be spirally wound, convolutely wound, or longitudinally seamed, to form an elongated cylinder. In some embodiments, the wall can be constructed using a smooth thin ply of material on the outer surface 34 of the insertion tube 12 that surrounds a coarser and possibly thicker ply.

If the wall contains at least three plies, the middle ply can be the thicker ply and the interior and exterior plies can be smooth and/or slippery to facilitate expulsion of the tampon and to facilitate insertion of the insertion tube 12 into a woman's vagina, respectively. The exterior plies do not have to be smooth in all instances. By sandwiching a thick, coarser ply of material between two thin, smooth plies, an inexpensive insertion tube 12 can be provided which is very functional. In certain embodiments, the wall may comprise one to four plies, although more plies or fewer plies can be utilized if desired. In some embodiments, the outer surface 34 of the insertion tube can be coated such that it has a smooth finish. Any suitable coating can be used to provide a smooth finish. Examples of suitable coatings include wax, polyethylene, a combination of wax and polyethylene, cellophane and clay, or any combinations thereof.

The plies, if any, forming the wall can be held together by an adhesive, such as glue, or by heat, pressure, ultrasonics, etc. The adhesive can be either water-soluble or water-insoluble. A water-soluble adhesive can be advantageous for environmental reasons. For example, a water-soluble adhesive can allow the wall to quickly break apart when it is immersed in water. Such immersion can occur should the insertion tube 12 be disposed of by flushing it down a toilet. Exposure of the insertion tube 12 to a municipal's waste treatment plant, e.g. exposure to chemicals, exposure to agitation, can cause the wall to break apart and evenly disperse in a relatively short period of time.

The plunger tube 14 can be configured similarly to the insertion tube 12 described heretofore. For example, the plunger tube 14 can be made from the same materials as the insertion tube. Additionally, the plunger tube 14, in some embodiments, can have a wall thickness which is similar to that of the insertion tube. Also, the plunger tube 14 may comprise a single ply of material or more than one ply similar to the insertion tube 12. In some embodiments, the plunger tube 14 is configured such that the plunger tube 14 is telescopically associated with the insertion tube 12.

Figure 2:
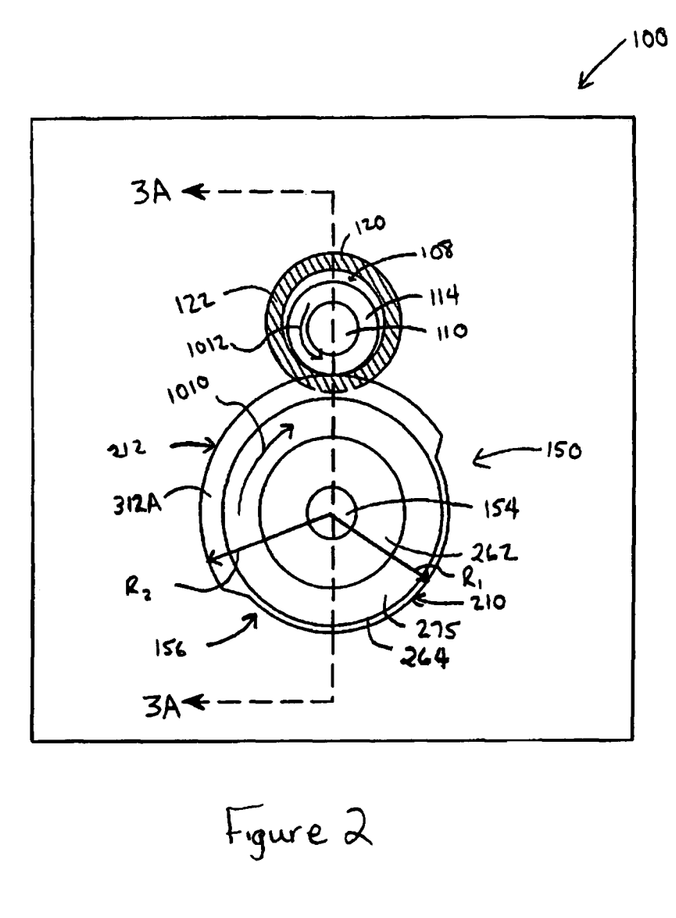
FIG. 2 is an elevation view showing an embossing assembly of the present invention which can be used to create the embossment of the plunger tube of FIG. 1.

As shown in FIG. 2, an embossing assembly 100 constructed in accordance with the present invention may be utilized to create the interlocking region 30 (shown in FIG. 1) of the plunger tube 14 (shown in FIG. 1). The embossing assembly 100 may comprise a first roll 108 and a second roll 150. The first roll 108 may comprise a first shaft 110 and an embossing element 114. In some embodiments, as shown, the embossing element 114 may surround the first shaft 110. In yet other embodiments, the embossing element 114 may comprise a plurality of discrete protrusions which extend outward from the first shaft 110. In some embodiments, the embossing element 114 comprises a smooth outer surface which engages a tube blank 120. As shown the first roll 108 may be configured such that the tube blank 120 can surround both the first shaft 110 and the embossing element 114.

The embossing element 114 can be configured in any suitable manner such that the engagement between the indented region 32 and the interlocking region 30 is achieved. For example, the embossing element 114 may comprise a cavity adjacent an outer perimeter of the embossing element 114 such that the interlocking region 30 of the plunger tube 14 extends inward from the outer surface of the plunger tube 14.

The tube blank 120 is a portion of an applicator which may not yet be embossed or may not yet be fully embossed. For example, the tube blank 120 may comprise the plunger tube 14 (shown in FIG. 1) before the interlocking region 30 (shown in FIG. 1) is embossed. The tube blank may comprise any suitable cross sectional shape. For example, the cross section of the tube blank 120 may be circular (shown in FIG. 2), elliptical, triangular, rectangular, rhomboidal, trapezoidal, or any other polygon.

The second roll 150 may comprise a second shaft 154 and a hub 156. The hub 156 can be joined to the second shaft 154. The hub 156 may comprise an engagement region 212 and a non-engagement region 210.

Figure 3A:
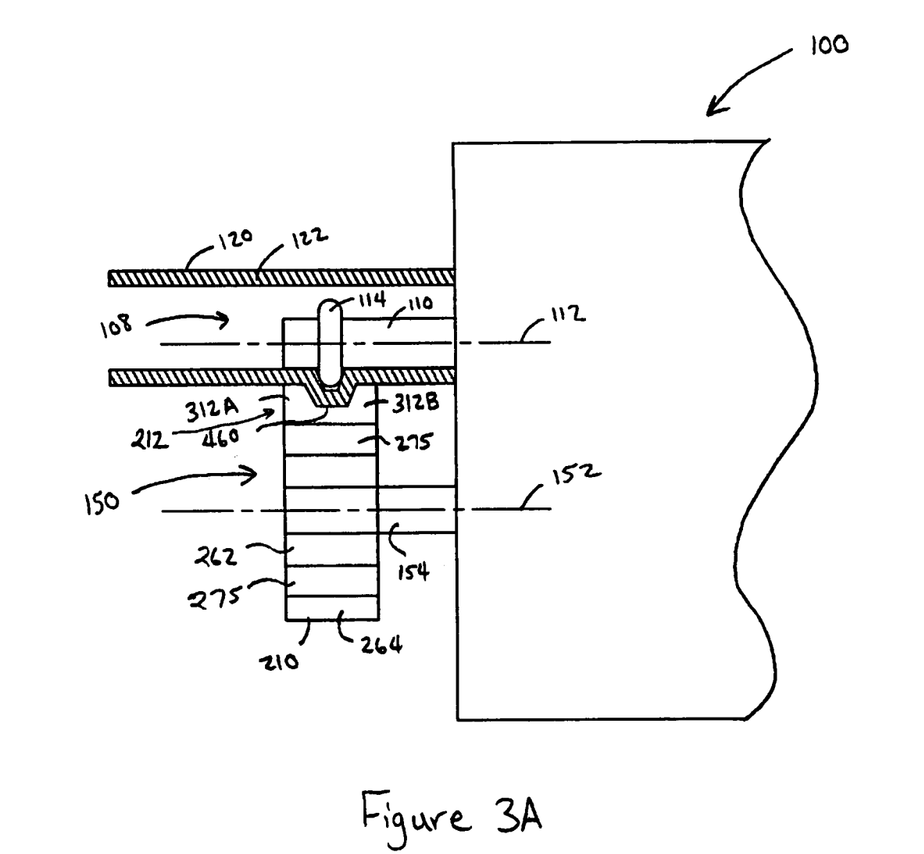
FIG. 3A is a cross sectional view through line 3A-3A showing the embossing assembly of FIG. 2.

As shown, in some embodiments, the engagement region 212 can be configured to receive the embossing element 114 between a pair of shoulders 312A and 312B (shown in FIG. 3A). As shown in FIG. 2, the engagement region 212 can be disposed outward from the second shaft 154 at an engagement radius $R_2$. In some embodiments, the engagement radius $R_2$ can be greater than a non-engagement radius $R_1$. The engagement region 212 can be configured to provide pressure to a wall 122 of the tube blank 120 adjacent the embossing element 114 thereby causing the wall 122 of the tube blank 120 to conform to the shape of the embossing element 114.

As shown, the non-engagement region 210 can be disposed outward from the second shaft 154 at the non-engagement radius $R_1$. In some embodiments, the non-engagement region 210 can be configured to apply no pressure to the wall 122 of the tube blank 120. In some embodiments, the non-engagement region 210 can be configured to apply less pressure to the wall 122 of the tube blank 120 than does the engagement region 212.

As shown in FIG. 2, the hub 156 may further comprise a compliant material 275 which is disposed adjacent to the engagement region 212. The compliant material 275 can allow part of the engagement region 212 to move with respect to the second shaft 154 such that the engagement region 212 can compensate for variable thicknesses in the wall 122 of the tube blank 120.

The compliant material 275, in some embodiments, can be more compliant than the second shaft 154. In some embodiments, the compliant material 275 can be more compliant than the first roll 108. In some embodiments, the compliant material 275 can be more compliant than an inner support 262 and/or an outer support 264. Exemplary orientations of the compliant materials are discussed hereafter with regard to FIGS. 4A-4B, 5, and 6.

As shown, in operation, the second roll 150 can rotate in a direction shown by arrow 1010 while the first roll 108 can rotate in a direction shown by arrow 1012. Embodiments where the second roll 150 rotates in the direction shown by arrow 1010 while the first roll 108 remains stationary are contemplated. Embodiments where the first roll 108 rotates in the direction shown by arrow 1012 while the second roll 150 is stationary are also contemplated.

In some embodiments, the engagement region 212 may comprise a portion of the second roll 150 which is defined by a sector which has an arc length equal to that of the engagement region 212. The non-engagement region 210 can be defined by the remaining sector which makes up the second roll 150. In some embodiments, the arc length of the engagement region 212 can be equal to about the perimeter of the tube blank 120. In some embodiments, the arc length of the engagement region 212 can be greater than the perimeter of the tube blank 120. In some embodiments, the arc length of the engagement region 212 can be less than the perimeter of the tube blank 120.

As shown in FIG. 3A, the first roll 108 can rotate about a first axis 112 while the second roll 150 can rotate about a second axis 152. In some embodiments, the first axis 112 and the second axis 152 are generally parallel.

Additionally, the engagement region 212 may comprise the pair of shoulders 312A and 312B and an engaging surface 460. As shown, in some embodiments, the compliant material 275 can be disposed between an outer support 264 and an inner support 262. The outer support 264, in some embodiments, may comprise a portion of the engagement region 212, e.g. the shoulders 312A, 312B, and engaging surface 460. Other exemplary orientations of the compliant material 275 within the anvil roll 150 are provided with regard to FIGS. 4A-4B, 5, and 6.

Because the compliant material 275 is disposed between the outer support 264 and the inner support 262, the engagement surface 460 can compensate for variations in the thickness of the wall 122 of a tube blank 120. For example, where the thickness of a part of the wall 122 is thicker than a preceding part of the wall 122, the engaging surface 460 and the pair of shoulders 312A and 312B can move inward (toward the second shaft 154). In contrast, in another example, when a subsequent part of the wall 122 is thinner than a previous part of the wall 122, the engaging surface 460 and the shoulders 312A and 312B can move outward (away from the second shaft 154).

Another advantage of the present invention is that a distance 375 (shown in FIG. 3B) between the embossing element 114 and the engaging surface 460 can be decreased versus conventional embossing processes. For example, in conventional embossing processes utilizing an all steel first roll, all steel embossing element, all steel first shaft, all steel second roll, all steel second shaft, and all steel hub, variations in the thickness of the wall 122 can cause pressure fluctuations. For example, a tube blank 120 having a wall 122 having a thickness of about 0.7 mm can experience higher pressures when engaged by the engaging region of the second roll when compared to a wall 122 having a thickness of about 0.5 mm. This higher pressure, in some instances, can be enough to cut through the material of the wall 122 thereby creating a defective part for an applicator. Consequently, the distance 375, in conventional embossing assemblies is typically greater than about 0.7 mm so that the number of tube blanks 120 which are cut through are reduced.

Figure 3B:
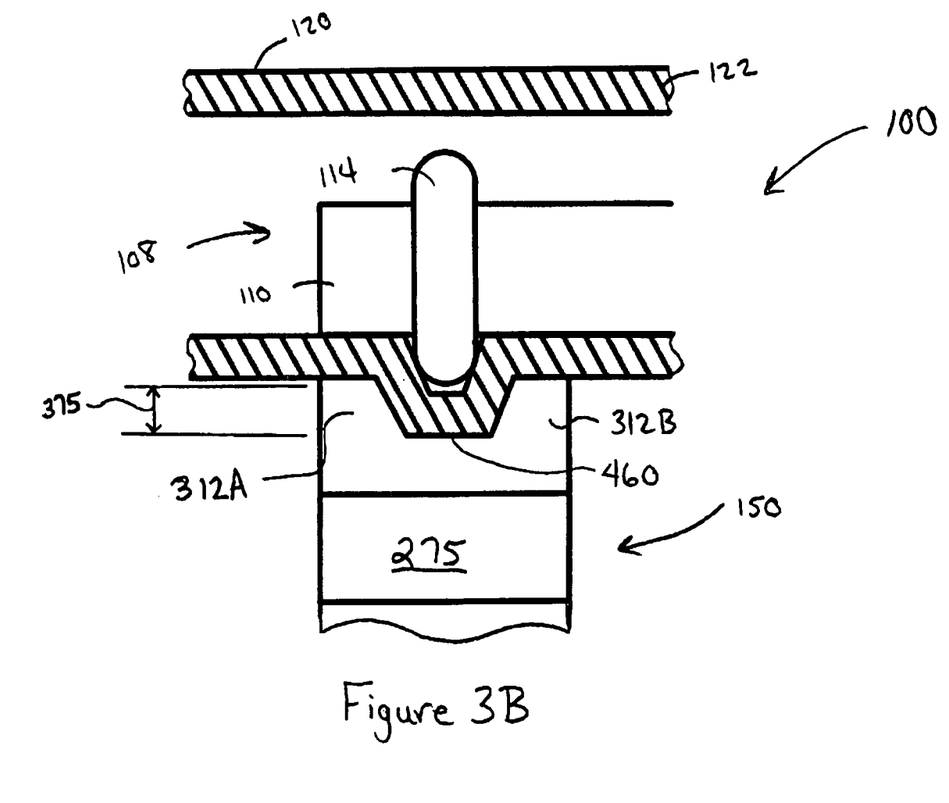
FIG. 3B is a close up view showing the embossing assembly of FIG. 3A.

In contrast, as shown in FIG. 3B, by implementing the embossing assembly 100 of the present invention, the distance 375 can be reduced to less than about 0.7 mm. If a wall 122 having a thickness of about 0.7 mm is engaged by the engagement region 212, then the compliant material 275 can allow the engagement region 212 to compensate for the increased thickness thereby reducing the pressure applied to the wall 122. Additionally, if a wall 122 having a thickness of less than about 0.7 mm is engaged by the engagement region 212, the decreased distance 375 can allow the first roll 108 and the second roll 150 to emboss the tube blank 120.

Additionally, by decreasing the distance 375, the interlocking region 30 (shown in FIG. 1) of the plunger tube 14 (shown in FIG. 1) can extend further outward from the outer surface 36 (shown in FIG. 1) of the plunger tube 14 (shown in FIG. 1). By increasing the interlocking region 30, the tube lock between an insertion tube and a plunger tube can be increased. Consequently, an embossing assembly constructed in accordance with the present invention can produce a plunger tube which has a reduced likelihood of becoming disengaged with the insertion tube.

The engagement region 212 can be configured to produce an interlocking region 30 (shown in FIG. 1) which is continuous or which is discontinuous. For example, in some embodiments, the interlocking region 30 (shown in FIG. 1) can be continuous about the circumference of the plunger tube 14 (shown in FIG. 1). In other embodiments, the interlocking region 30 (shown in FIG. 1) can be discontinuous about the circumference of the plunger tube 14 (shown in FIG. 1). Additionally, in some embodiments, the engagement region 212 can be configured to produce a spiral interlocking region 30 (shown in FIG. 1) on the plunger tube 14 (shown in FIG. 1).

As shown in FIGS. 4A-4B, 5 and 6, the compliant material 275 can be oriented within the second roll 150 in a number of different configurations. The compliant material 275 can be disposed within embossing assembly 100 (shown in FIGS. 2, 3A, and 3B) in any suitable configuration which allows the embossing assembly 100 (shown in FIGS. 2, 3A, and 3B) to compensate for the variability in thicknesses of the wall 122 of the tube blank 120. For example, in some embodiments, the compliant material 275 can be disposed outward from the second shaft 154 and can surround the second shaft 154, as shown in FIG. 2. In other embodiments, the compliant material 275 can be disposed adjacent to the engagement region 212 while not being disposed in the non-engagement region 210.

Figure 4A:
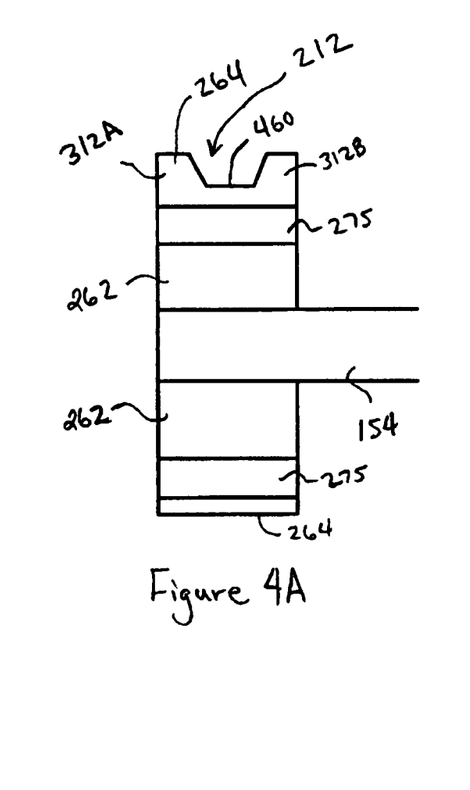
FIG. 4A is a close up of a cross sectional view showing the anvil roll of FIG. 3A.
Figure 4B:
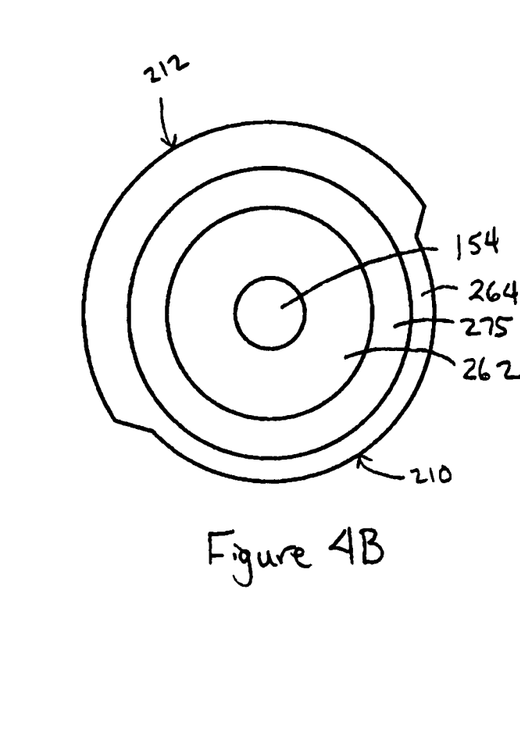
FIG. 4B is an elevation view showing the anvil roll of FIG. 4A.

As shown in FIGS. 4A and 4B, in some embodiments, the outer support 264 may comprise the pair of shoulders 312A and 312B and the engagement surface 460. In embodiments where the outer support 264 comprises the shoulders 312A and 312B and the engagement surface 460, edges of the interlocking region 30 (shown in FIG. 1) can be more defined as opposed to embodiments where the shoulders 312A and 312B comprise the compliant material 275.

Also, as shown, in some embodiments, the compliant material 275 can be disposed between the outer support 264 and the inner support 262. In some embodiments, the outer support 264 can surround the inner support 262. In some embodiments, the outer support 264 can partially surround the inner support 262. Similarly, in some embodiments, the compliant material 275 can be disposed between the outer support 264 and the inner support 262 such that the compliant material surrounds the inner support 262. In other embodiments, the compliant material 275 can be disposed between the outer support 264 and the inner support 262 such that the compliant material 275 surrounds only a portion of the inner support 262. In some embodiments, the compliant material 275 can be continuously applied about the perimeter of the inner support 262. In other embodiments, the compliant material 275 can be applied in a plurality of discrete elements which are disposed about the perimeter of the inner support 262.

Figure 5:
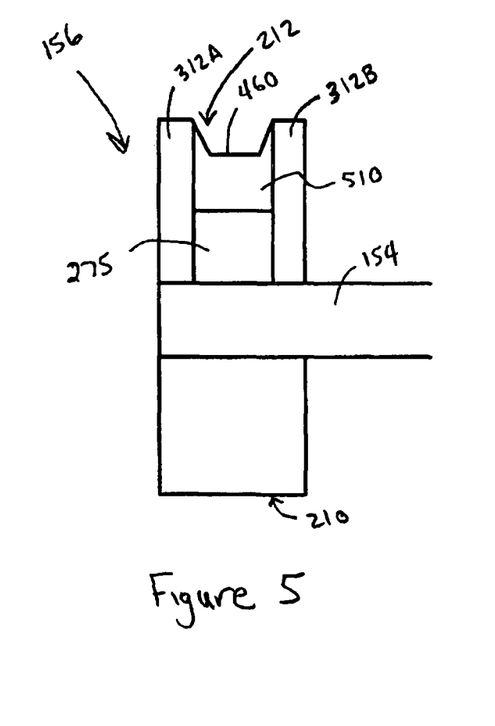
FIG. 5 is a close up of a cross sectional view showing another embodiment of an anvil roll which can be used in the present invention.

As shown in FIG. 5, in some embodiments, the hub 156 may comprise an engaging element 510 which forms a portion of the engaging surface 460. The engaging element 510 can be disposed between the pair of shoulders 312A and 312B. The pair of shoulders 312A and 312B, in some embodiments, may be joined to the second shaft 154 and form a cavity between the shoulders 312A and 312B. The engaging element 510 can be disposed within the cavity. The compliant material 275, in some embodiments, can be disposed between the second shaft 154 and the engaging element 510 within the cavity.

Figure 6:
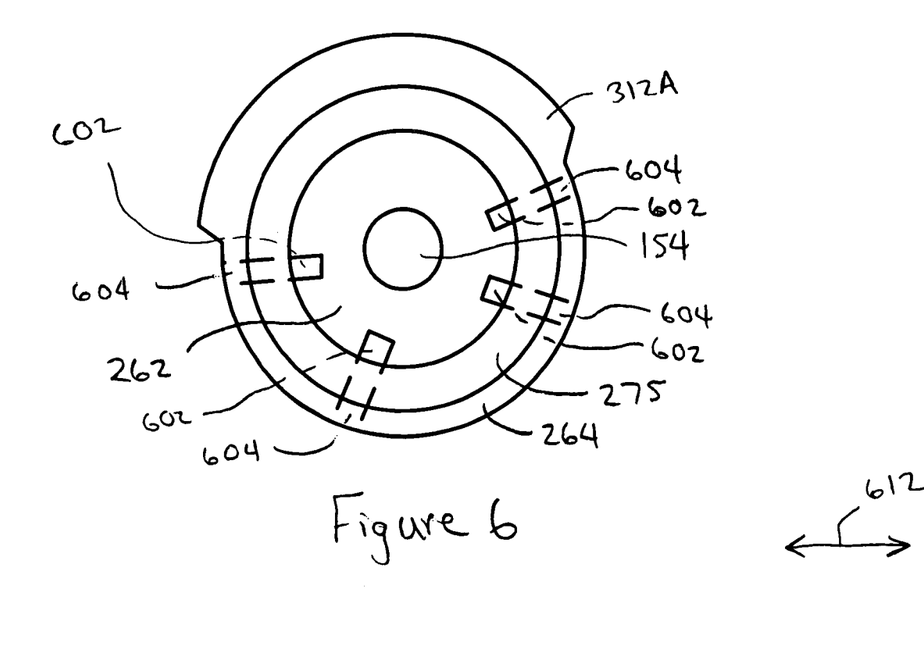
FIG. 6 is an elevation view showing another embodiment of an anvil roll which can be used in the present invention.

As shown in FIG. 6, in some embodiments, the compliant material 275 can be disposed between the outer support 264 and the inner support 262, similar to the configuration shown in FIG. 4A. However, in some embodiments, as shown, the compliant material 275 may include inner stabilizers 602 and/or outer stabilizers 604. The inner stabilizers 602, in some embodiments, can extend inward toward second shaft 154 thereby providing lateral stabilization to the compliant material 275. In some embodiments, the outer stabilizers 604 can extend outward toward the outer support 264 thereby providing lateral stabilization to the compliant material 275.

In some embodiments, the outer stabilizers 604 can be configured such that they do not extend into the engaging surface 460 (shown in FIGS. 3A, 3B, 4A, and 5). Alternatively, in some embodiments, the outer stabilizers 604 can be configured such that they extend into the engaging surface 460 (shown in FIGS. 3A, 3B, 4A, and 5).

Any suitable number of inner and/or outer stabilizers can be used in order to provide lateral stabilization to the compliant material 275. For example, in some embodiments, the compliant material 275 may comprise four inner stabilizers 602 and four outer stabilizers 604. The lateral direction is shown by dual arrow 612 and can be generally parallel to the axis of rotation 152 (shown in FIG. 3A) of the second roll 156.

Any suitable material can be utilized for the inner and/or outer stabilizers. For example, in some embodiments, the inner and/or outer stabilizers may comprise the compliant material 275. In some embodiments, the inner and/or outer stabilizers may comprise stainless steel.

Embodiments where the first roll 108 comprises a compliant material are contemplated. For example, in some embodiments, the first shaft 110 and/or the embossing element 114 may comprise a compliant material.

The first roll 108, the first shaft 110, and the embossing element 114 can be formed from any suitable material used for embossing. For example, in some embodiments, the first shaft 110 and/or the embossing element 114 can be formed from steel, e.g. stainless steel, aluminum, or the like.

Similarly, the second shaft 154 can be formed from any suitable material. For example, in some embodiments, the second shaft 154 may comprise steel, e.g. stainless steel, aluminum, the like or suitable combinations thereof.

The inner support 262 and/or the outer support 264 can be formed of any suitable material known in the art. For example, the inner support 262 and/or the outer support 264 may comprise steel, e.g. stainless steel, aluminum, the like, or suitable combinations thereof. In yet another example, the inner support 262 may be formed partially from a first material and partially from a second material. The first material can be, for example, steel, while the second material can be for example, a compliant material 275. In yet another example, the inner support 262 may be formed from compliant material 275. In some embodiments, the outer support 264 can be configured similarly to the inner support 262.

The engagement surface 460 can be formed from any suitable material known in the art. For example, the engagement surface 460 can be formed from steel, e.g. stainless steel, aluminum, the like, or suitable combinations thereof. In yet another example, the engagement surface 460 can be formed from the compliant material 275. In yet another example, the engagement surface 460 can be formed partially from a first material and partially from a second material. The first material, for example, can be steel, while the second material can be, for example, the compliant material 275.

Similarly, the shoulders 312A and 312B can be formed from any suitable material. For example, the shoulders 312A and 312B can be formed from steel, e.g. stainless steel, aluminum, or the like. In yet another example, the shoulders 312A and 312B can be formed from the compliant material 275. In yet another example, the shoulders 312A and/or 312B can be formed from a first material and a second material. The first material, for example, can be steel, while the second material can be, for example, the compliant material 275.

The compliant material 275 of the present invention may comprise any suitable compliant material known in the art. Some examples of compliant materials are disclosed in U.S. Pat. No. 6,170,393. In some embodiments, the compliant material can have a durometer of between about 30 Shore A to about 100 Shore A or any individual number within the range. In other embodiments, the compliant material can have a durometer of between about 50 Shore A to about 95 Shore A. In yet other embodiments, the compliant material can have a durometer of between about 80 Shore A to about 95 Shore A. In yet other embodiments, the compliant material can have a durometer of about 75 Shore D. Durometers are measured in accordance with ASTM D2240.

In some embodiments, the compliant material can be poured and formed through a compression mold. In some embodiments, the compliant material can be machined, glued, etc.

EXAMPLE

An exemplary second roll was created in accordance with the present invention. The anvil roll was configured similar to the anvil roll shown in FIG. 6. The compliant material 275 was disposed between the outer support 264 and the inner support 262. The compliant material 275 was applied at a thickness 610 of about 4.75 mm. The compliant material 275 had a durometer of 95 Shore A and was manufactured by Omni Technologies, Greenfield, Ind. The compliant material 275 was poured and formed through a compression mold.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. An embossing assembly for forming an embossment pattern on a tube blank, the embossing assembly comprising:
   a) a first roll comprising:
      i) a first shaft; and
      ii) an embossing element joined to the first shaft, wherein the embossing element extends outward from and surrounds the first shaft, the first shaft and embossing element being configured such that a tampon applicator tube blank can at least partially surround the first shaft and the embossing element; and
   b) a second roll, configured to engage the tampon applicator tube blank, wherein the second roll comprises a second shaft and a hub joined to the second shaft, wherein the hub comprises:
      i) an engagement region disposed outward from the second shaft, wherein the engagement region is configured to apply pressure to the tampon applicator tube blank adjacent to the embossing element thereby causing part of the tampon applicator tube blank to at least partially conform to the shape of the embossing element, and wherein the engagement region has an arc length greater than a diameter of the embossing element;
      ii) a non-engagement region disposed outward from the second shaft, wherein the non-engagement region transitions into the engagement region at two places about a circumference of the outer support, and wherein the engagement region and the non-engagement region together surround the second roll; and
      iii) an inner support joined to the second shaft such that the inner support at least partially surrounds the second shaft, an outer support joined to the inner support such that the outer support at least partially surrounds the inner support, and a compliant material disposed between the outer support and the inner support, wherein the outer support comprises at least a portion of the engagement region, and wherein the compliant material is more compliant than the outer support.

2. The embossing assembly of claim 1, wherein the compliant material has a durometer of from 30 Shore A to 100 Shore A.

3. The embossing assembly of claim 1, wherein the compliant material has a durometer of from 80 Shore A to 95 Shore A.

4. The embossing assembly of claim 1, wherein the engagement region comprises a pair of shoulders and an engaging surface, wherein the embossing element is received between the pair of shoulders.

5. The embossing assembly of claim 1, wherein the first roll rotates about a first axis of rotation and the second roll rotates about a second axis of rotation, and wherein the first axis of rotation is generally parallel to the second axis of rotation.

6. The embossing assembly of claim 1, wherein the tube blank fully surrounds the first shaft and the embossing element.

7. An embossing assembly for forming an embossment pattern on a tube blank, the embossing assembly comprising:
   a) a first roll comprising:
      i) a first shaft having a first axis of rotation; and ii) an embossing element joined to the first shaft, wherein the embossing element extends outward from and surrounds the first shaft, the first shaft and embossing element being configured such that a tampon applicator tube blank can at least partially surround the first shaft and the embossing element; and b) a second roll having a second axis of rotation, wherein the first axis and the second axis are generally parallel, wherein the second roll is configured to engage the tampon applicator tube blank, wherein the second roll comprises a second shaft and a hub joined to the second shaft, wherein the hub comprises:

i) an engagement region disposed outward from the second shaft, wherein the engagement region is configured to apply pressure to the tampon applicator tube blank adjacent to the embossing element thereby causing part of the tampon applicator tube blank to at least partially conform to the shape of the embossing element, and wherein the engagement region has an arc length greater than a diameter of the embossing element;

ii) a non-engagement region disposed outward from the second shaft, wherein the non-engagement region transitions into the engagement region at two places about a circumference of the outer support, and wherein the engagement region and the non-engagement region together surround the second roll and, iii) an inner support joined to the second shaft such that the inner support at least partially surrounds the second shaft, an outer support joined to the inner support such that the outer support at least partially surrounds the inner support, and a compliant material having a durometer of about 75 Shore D disposed between the outer support and the inner support, wherein the outer support comprises at least a portion of the engagement region, and wherein the compliant material is more compliant than the outer support.

8. The embossing assembly of claim 7, wherein the engagement region comprises a pair of shoulders and an engaging surface, wherein the embossing element is received between the pair of shoulders.

9. The embossing assembly of claim 7, wherein the tube blank fully surrounds the first shaft and the embossing element.

10. An embossing assembly for forming an embossment pattern on a tube blank, the embossing assembly comprising:

a) a first roll comprising:

i) a first shaft having a first axis of rotation; and ii) an embossing element joined to the first shaft, wherein the embossing element extends outward from and surrounds the first shaft, the first shaft and embossing element being configured such that a tampon applicator tube blank can at least partially surround the first shaft and the embossing element; and b) a second roll having a second axis of rotation, wherein the first axis and the second axis are generally parallel, wherein the second roll is configured to engage the tampon applicator tube blank surrounding the first roll, wherein the second roll comprises a second shaft and a hub joined to the second shaft, wherein the hub comprises:

i) an inner support joined to the second shaft;

ii.) a compliant material joined to and disposed outward from the inner support, wherein the compliant material has a durometer of about 95 Shore A;

iii) an outer support joined to and disposed outward from the compliant material, wherein the outer support comprises a pair of shoulders and an engaging surface, wherein the embossing element is received between the shoulders;

iv) an inner lateral stabilizer extending from the compliant material through the inner support, wherein the compliant material is more compliant than the outer support;

v) an engagement region disposed outward from the second shaft, wherein the engagement region is configured to apply pressure to the tampon applicator tube blank adjacent to the embossing element thereby causing part of the tampon applicator tube blank to at least partially conform to the shape of the embossing element, and wherein the engagement region has an arc length greater than a diameter of the embossing element; and vi) a non-engagement region disposed outward from the second shaft, wherein the non-engagement region transitions into the engagement region at two places about a circumference of the outer support, and wherein the engagement region and the non-engagement region surround the second roll.

11. The embossing assembly of claim 10, wherein one of the shoulders comprises a second compliant material.

12. The embossing assembly of claim 10, wherein the hub further comprises an outer lateral stabilizer extending from the compliant material outward through the outer support.

13. The embossing assembly of claim 10, wherein the tube blank fully surrounds the first shaft and the embossing element.

* * * * *